(12) United States Patent
Lesci

(10) Patent No.: US 11,446,644 B2
(45) Date of Patent: Sep. 20, 2022

(54) PHOTOCATALYTIC CERAMIC

(71) Applicant: ITALCER S.p.A., Rubiera (IT)

(72) Inventor: Isidoro Giorgio Lesci, Castel Bolognese (IT)

(73) Assignee: ITALCER S.p.A., Rubiera (IT)

( * ) Notice: Subject to any disclaimer, the term of this patent is extended or adjusted under 35 U.S.C. 154(b) by 53 days.

(21) Appl. No.: 17/012,303

(22) Filed: Sep. 4, 2020

(65) Prior Publication Data

US 2021/0069681 A1 Mar. 11, 2021

(30) Foreign Application Priority Data

Sep. 5, 2019 (IT) .................. 102019000015677

(51) Int. Cl.
*B01J 27/18* (2006.01)
*B01J 21/06* (2006.01)
(Continued)

(52) U.S. Cl.
CPC ......... *B01J 27/1806* (2013.01); *B01J 21/063* (2013.01); *B01J 35/004* (2013.01);
(Continued)

(58) Field of Classification Search
CPC .... B01J 27/1806; B01J 21/063; B01J 35/004; B01J 37/0215; B01J 37/04; B01J 37/08;
(Continued)

(56) References Cited

U.S. PATENT DOCUMENTS

2007/0215006 A1* 9/2007 Naganuma ............. C04B 41/00
106/462

FOREIGN PATENT DOCUMENTS

EP      1 304 366 B2    10/2012
JP        H10363 A *   1/1998
(Continued)

OTHER PUBLICATIONS

Nathanael etal (Mechanical and photocatalytic properties of hydroxyapatite/titania nanocomposites prepared by combined high gravity and hydrothermal process, ELSEVIER, Nov. 13, 2009) (Year: 2009).*

(Continued)

*Primary Examiner* — Anthony J Zimmer
*Assistant Examiner* — Logan Edward Laclair
(74) *Attorney, Agent, or Firm* — Oblon, McClelland, Maier & Neustadt, L.L.P.

(57) ABSTRACT

The present invention relates to a method for producing an antibacterial photocatalytic ceramic that comprises:
  making available amorphous Ti;
  making available a biomimetic material or a biomaterial based on calcium phosphate;
  functionalizing said biomimetic material or said biomaterial based on calcium phosphate, with said amorphous Ti, obtaining a functionalized and oriented composite;
  adding said functionalized composite to a ceramic mixture, and/or applying said functionalized composite on a ceramic semi-finished product, where ceramic semi-finished product means the ceramic material before baking;
  applying said functionalized composite on a ceramic semi-finished product;
  baking at a temperature between 600 and 1400° C., preferably between 900 and 1300° C., for a time that varies from 20 to 500 minutes, obtaining an antibacterial photocatalytic ceramic.

The present invention further relates to a photocatalytic ceramic material that comprises a biomimetic material having a nanostructured hierarchical structure with macro and micro cavities, within which $TiO_2$ is included in the crystalline form of rutile, and tiles, sanitary ware and tableware comprising same.

10 Claims, 6 Drawing Sheets

(51) Int. Cl.
    *B01J 35/00*    (2006.01)
    *B01J 37/02*    (2006.01)
    *B01J 37/04*    (2006.01)
    *B01J 37/08*    (2006.01)

(52) U.S. Cl.
    CPC .......... *B01J 37/0215* (2013.01); *B01J 37/04* (2013.01); *B01J 37/08* (2013.01)

(58) Field of Classification Search
    CPC .... B01J 35/002; B01J 35/006; B01J 37/0009; B01J 37/038; A61L 2/088; C01B 25/322; C01B 25/327; C04B 2235/3212; C04B 33/34; C04B 2235/3232; C04B 41/009; C04B 41/4584; C04B 41/5048; C04B 2111/00827; C04B 41/87; C04B 35/447; C04B 41/5022; C04B 41/86; C04B 2235/3217
    See application file for complete search history.

(56) References Cited

FOREIGN PATENT DOCUMENTS

| | | |
|---|---|---|
| JP | 2017-71515 A | 4/2017 |
| WO | WO 2010/14641 | 12/2010 |

OTHER PUBLICATIONS

European Search Report dated May 15, 2020 in Italian Patent Application No. 201900015677, 2 pages.

Tim Luttrell, et al., "Why is anatase a better photocatalyst than rutile?—Model studies on epitaxial $TiO_2$ films," Scientific Reports, vol. 4, No. 4043, 2014, 8 pages.

Won Young Jung, et al., "Synthesis of Ti-containing SBA-15 materials and studies on their photocatalytic decomposition of orange II," Catalysis Today, vol. 131, 2008, pp. 437-443.

N.B. Lihitkar, et al., "Titania nanoparticles synthesis in mesoporous molecular sieve MCM-41" Journal of Colloid and Interface Science, vol. 314, 2007, pp. 310-316.

Shigeru Ikeda, et al., "Structural effects of titanium (IV) oxide encapsulated in a hollow silica shell on photocatalytic activity for gas-phase decomposition of organics," Applied Catalysis A: General, vol. 369, 2009, pp. 113-118.

K.M. Parida, et al., "Synthesis of mesoporous $TiO_{2-x}N_x$ spheres by template free homogeneous co-precipitation method and their photo-catalytic activity under visible light illumination," Journal of Colloid and Interface Science, vol. 333, 2009, pp. 269-276.

Hiroshi Irie, et al., "Nitrogen-Concentration Dependence on Photocatalytic Activity of $TiO_{2-x}N_x$ Powders," J. Phys. Chem. B, vol. 1 07, 2003, pp. 5483-5486.

R. Asahi, et al., "Visible-Light Photocatalysis in Nitrogen-Doped Titanium Oxides," Science, vol. 293, Jul. 13, 2001, pp. 269-271.

C Jeffrey Brinker, "Oriented inorganic films," Current Opinion in Colloid & Interface Science, vol. 3, 1998, pp. 166-173.

* cited by examiner

Electron Image 1

PHOTOCATALYTIC CERAMIC

PRIOR ART

Ceramics are among the most used materials in buildings and, with ever increasing interest, are encountered in the field of fittings, used as coverings and/or as constructional elements for making hard parts in the kitchen and bath fittings sector (for example counter top and/or backsplash). Uses range from the residential sector to hospitality, and research laboratories.

The use of ceramic materials having antimicrobial properties has obvious advantages. Photocatalysis is the natural phenomenon by which a photocatalyst produces a strong oxidation process that decomposes organic and inorganic contaminants, transforming them into harmless substances. Titanium dioxide $TiO_2$ stands out among the materials most studied in photocatalysis. $TiO_2$ combines long-term stability and low toxicity for the biosphere with good photocatalytic activity. The photocatalytic properties of $TiO_2$ have been investigated in recent years on a wide range of pollutants, both of the atmosphere and of water: alcohols, halides, aromatic hydrocarbons. The studies conducted have given promising results for organic acids, dyes, $NO_x$ and others. For these reasons $TiO_2$ is already widely used in surface treatment.

These properties of $TiO_2$ have been applied in the removal of bacteria and harmful organic materials in water and in the air, as well as on surfaces, particularly in medical/hospital settings. The activity of $TiO_2$ is influenced by a variety of factors, such as crystalline structure, the surface, the size distribution of the nanoparticles, porosity, number and density of hydroxyl groups on the surface of the $TiO_2$.

$TiO_2$ in fact occurs in amorphous form or in crystalline forms, and the amorphous form is photocatalytically inactive. Three natural crystalline forms of $TiO_2$ are known, called anatase, rutile and brookite. Anatase and rutile have a tetragonal structure, while the structure of brookite is orthorhombic. Brookite is the less common form. Anatase and rutile are photocatalytically active, while brookite has never been tested for photocatalytic activity. Pure anatase is more active as a photocatalyst compared to rutile, probably because it has a higher negative potential at the edge of the conduction band, which means higher potential energy of photogeneration of electrons, and a higher number of hydroxyl groups on its surface.

Luttrell T. et al., Scientific Reports 4, Article number 4043, 2014, describe that the higher or lower photocatalytic activity of rutile and anatase might depend on the properties of the surface on which they are deposited and on the thickness of the coating deposited on the surface. For example, with identical surface conditions, anatase reaches its maximum activity if the coating is thicker than 5 nm, while for rutile a coating of 2.5 nm is sufficient. This activity can be increased by doping $TiO_2$ appropriately. In recent years the scientific literature has been enriched with detailed studies on the doping of $TiO_2$ with metal oxides.

On calcining in the range 300-500° C., formation of pure anatase is observed. With increasing temperature, an increase in the size of the crystals is observed. On calcining between 500-700° C., a mixed anatase-rutile is obtained.

Some research groups (Jung W. Y. et al., Synthesis of Ti-containing SBA-15 materials and studies on their photocatalytic decomposition of orange II. Catal. Today, 131:437-443, 2008. Lihitkar N. B. et al., Titania nanoparticles synthesis in mesoporous molecular sieve MCM-41. J. Colloid Interface Sci., 314: 310-316, 2007. Ikeda S. et al., Structural effects of titanium (IV) oxide encapsulated in a hollow silica shell on photocatalytic activity for gas-phase decomposition of organics. Appl. Cat. A: General, 369: 113-118, 2009) focused their attention on the possibility of increasing the photoactivity of $TiO_2$ by increasing its surface area, thereby increasing the number of molecules adsorbed on its surface and promoting the charge transfer process.

The introduction of the photocatalyst on another material leads to an advantage of a practical nature. In fact, immobilization on a support inhibits or slows sintering of the particles, which is the cause of a decrease in surface area.

A further methodology used for increasing the activity of $TiO_2$ relates to the possibility of acting upon the electronic levels of the semiconductor, decreasing the energy of the band-gap so as to be able to use light at a lower frequency than the visible, to promote the electrons from the valence band (VB) to the conduction band (CB) (Parida K. M., Naik B. Synthesis of mesoporous TiO2-xNx spheres by template free homogeneous co-precipitation method and their photocatalytic activity under visible light illumination. J. Colloid Interface Sci., 333: 269-276, 2009. Irie H. et al., Nitrogen-Concentration Dependence on Photocatalytic Activity of TiO2-xNx Powders. J. Phys. Chem. B, 107: 5483-5486, 2003. Asahi R. et al., Visible-light photocatalysis in nitrogen-doped titanium oxides. Science, 293. 269-271, 2001). This methodology envisages modification of the material by doping and consists of introducing, in the synthesis step, suitable precursors of elements capable of modulating its electronic properties.

From the electronic viewpoint, $TiO_2$ is an n-type semiconductor; the value of Eg of anatase is equal to 3.2 eV, that of rutile 3.0 eV. From these values, we find, from equation (1):

$$Eg=h\ v=hc/\lambda=1240/\lambda \tag{1}$$

that anatase is "activated" by light having a wavelength A 388 nm, i.e. from the UVA portion of the electromagnetic spectrum, while rutile has $\lambda \leq 413$ nm, therefore light in the visible region (PAR, 400-700 nm). In equation (1), h represents Planck's constant, v is the frequency of the incident radiation and c is the speed of light in a vacuum; the product hc, a constant, is expressed in [eV×nm] and the wavelength A in nm.

WO2010146410A1 describes baking of the ceramic base at a temperature between 900 and 1250° C. and then using micrometric, crystalline $TiO_2$ dispersed in water in post-baking, to obtain a surface layer, under which a layer of adhesive is deposited. A subsequent heat treatment at 600° C. allows softening of the adhesive but not conversion of anatase to rutile, considered insufficiently photoactive.

EP1304366B2 describes the deposition of a layer of amorphous titanium on surfaces, generally vitreous. Subsequent baking of the material at a maximum temperature of 525° C. transforms the amorphous titanium to anatase.

Biomimetics is a multidisciplinary science in which biological processes are utilized for designing new "smart" materials or structures. For example, nature supplies soft and hard materials whose peculiar functional properties depend on the hierarchical organization of the fundamental molecular units constituting them at the level of the macro- and nano-scale.

There is a strongly perceived need for a ceramic material with high antibacterial activity, obtainable using an economically sustainable production process.

DESCRIPTION OF THE INVENTION

In the present invention, a "bio-inspired" ceramic surface is produced, formed from a new material with a hierarchical structure that is modelled on the structure of bone, with micro and macro cavities, and with micrometric dimensions, nano-structured and biocompatible, where $TiO_2$, of the rutile type, is formed at high temperatures on an inorganic support suitable for producing crystals with dimensions, morphology, structure and orientation such as to make the photocatalytic properties thereof particularly advantageous.

Definitions

Here, the terms "ceramic" or "ceramic material" or "ceramic product" mean the material and the finished product consisting thereof. Among the finished products, coating and covering materials, such as tiles and roofing-tiles, sanitary ware, and tableware, are highlighted here, as being of particular interest for the aims of the present invention.

Here, the term "oriented functionalized composite", or "composite", means a biomimetic material that comprises rutile arranged in an orderly manner, i.e. with a regular crystallographic arrangement relative to the substrate, where substrate means said biomimetic material (Brinker C. J. 1998 Current Opinion in Colloid & Interface Science. 3: 166-173).

Here, the term "ceramic semifinished product" means the ceramic material after the steps of moulding and, optionally, drying, which typically precede the baking process.

The term "coated ceramic semi-finished product" means the ceramic material as mentioned above, on which a mixture has been applied that comprises the oriented functionalized composite according to the present invention.

Here, the term "ceramic mixture" means the mixture of raw materials which, on moulding, will constitute the ceramic semi-finished product and hence the ceramic article.

The term "enriched ceramic mixture" means a ceramic mixture that comprises the oriented functionalized composite according to the present invention.

DESCRIPTION OF THE FIGURES

FIGS. 3C, 3D and 3E: surface localization of the P, Ca and Ti atoms, respectively, in the surface mapping.

FIG. 4A: hydroxyapatite microcrystals; FIG. 4B: photograph highlighting the nanostructured hierarchical structure; and FIGS. 4C and 4D: EDS microanalysis spectrum.

The present invention relates firstly to a method for producing an antibacterial photocatalytic ceramic that comprises:
making available amorphous titanium (amorphous Ti);
making available a biomimetic material and/or a biomaterial based on calcium phosphate;
functionalizing said biomimetic material and/or said biomaterial based on calcium phosphate with said amorphous Ti, obtaining a functionalized and oriented composite;
adding said functionalized composite to a ceramic mixture, and/or applying said functionalized composite on a ceramic semi-finished product, where ceramic semi-finished product means the ceramic material before baking;
baking at a temperature between 600 and 1400° C., preferably between 900 and 1300° for a time that varies from 20 to 500 minutes, obtaining an antibacterial photocatalytic ceramic.

In one embodiment, said amorphous Ti is selected from the group that comprises titanium(IV) oxysulphate, titanium tetrachloride, titanium tetraisopropoxide, titanium isopropoxide, titanium oxychloride.

Said material, synthetic (biomimetic) or of natural origin (biomaterial), is preferably selected from the group that comprises brushite, monetite, hydroxyapatite (HA), (p/a) tricalcium phosphate (TCP). Said material is calcium-deficient on the surface.

In a preferred embodiment, said material is nanocrystalline hydroxyapatite (nHA). Said hydroxyapatite is advantageously obtained at a pH between 7 and 14, preferably at pH 11, by neutralizing a suspension of calcium hydroxide or calcium acetate or calcium chloride or calcium nitrate drop by drop with phosphoric acid under vigorous stirring for 2-12 hours. The synthesis envisages a molar ratio between surface Ca/P of between 1.55 and 1.70, preferably 1.64.

Figure 1:
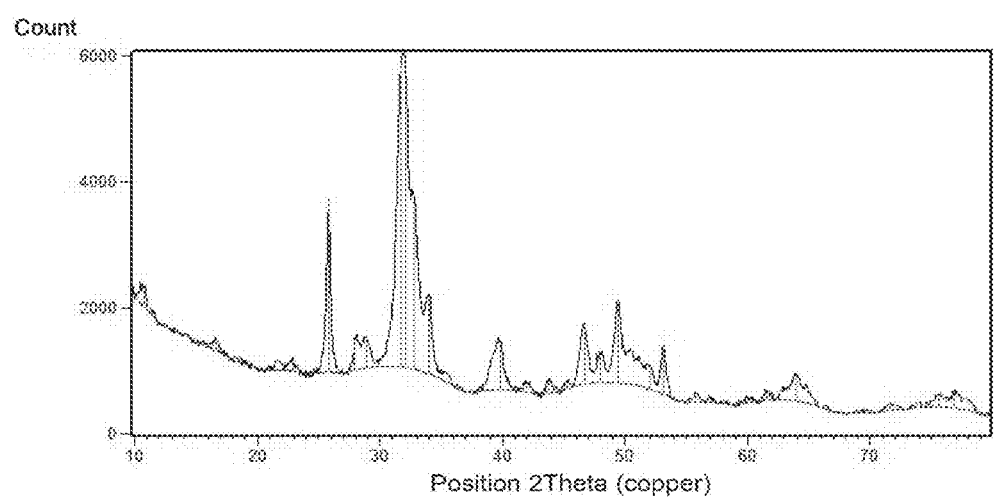
FIG. 1: X-ray diffraction spectrum of nHA.
Figure 2:
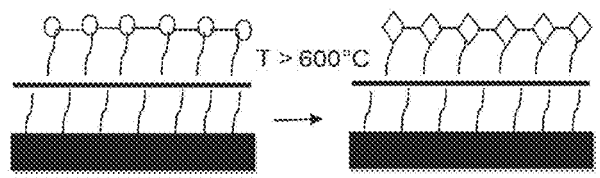
FIG. 2: schematic diagram of an embodiment of the surface functionalization process according to the present invention. The dots indicate amorphous Ti, and the diamonds indicate Ti in the rutile crystalline form. The black strip is the ceramic substrate, and the line represents the biomaterial or the biomimetic material.

FIG. 1 shows the diffraction spectrum of nHA thus obtained, showing that it is a crystalline material that has the diffraction maxima characteristic of hydroxyapatite. Said nHA exposes both positive and negative charges at the surface, which make it particularly reactive. This indicates that said nHA is able to bind quantities of amorphous titanium and to bond to the components of the ceramic semi-finished product.

In one embodiment, said functionalization is effected by adding said amorphous Ti dropwise to a solution of calcium phosphate in the form of brushite and/or monetite, in the case of acid hydrolysis (pH 1-6), or in the form of nHA or (β/α) TCP, in the case of basic hydrolysis (pH 7-14). Preferably, said amorphous Ti is added dropwise in an amount of 10-30 wt % relative to the volume of the hydrolysis solution, preferably of 15%, and said dropwise addition takes place under vigorous stirring for 2-12 hours.

In one embodiment, said functionalization is effected with doped titanium and said amorphous Ti is added dropwise in suspension with one or more metal ions selected from Cu, Zn, Ag, Sr, Al, Sb, W, Mn, Sn, V, Cr, Zr, Mo, Pd, preferably solvated. In one embodiment, said metal ions are solvated with 10-30% of isopropyl alcohol or, alternatively, ethyl alcohol.

In one embodiment, at least two metal ions are present. Preferably, said two metal ions are in 1/1 ratio to one another.

In one embodiment, said suspension comprises 10-30% (w/v) of said amorphous Ti and 0.1-0.5% (w/v) of said one or more solvated metal ions.

After said functionalization, the composite that is obtained is a functionalized and oriented composite, i.e. a material characterized by a regular crystallographic arrangement. Said biomimetic materials or biomaterials in fact consist of a structure of tetrahedra of $PO_4^{3-}$, and two oxygen atoms are on the horizontal plane. The present inventors have demonstrated, surprisingly, that said amorphous Ti binds the oxygens arranged on said horizontal plane and, following exposure to temperatures above 600° C., preferably above 900° C., there is formation of crystals of rutile, which grow in an ordered direction, determined by said deposit of amorphous Ti on said plane.

Said functionalized composite is applied on a ceramic semi-finished product to give a coated ceramic semi-finished product. As an example, said oriented functionalized composite is applied simultaneously with one or more glazing applications, or mixed with engobe applied after the forming step, or between one or more glazing applications. Moreover, said composite is applied during the process of screen printing, or of salt glazing, where present. By way of example, said composite is mixed with engobe, preferably in a ratio of 10-50% w/v, and then applied on the ceramic semi-finished product. Said engobe is selected from the engobes known in the ceramic sector, it is preferably a mixture that comprises kaolin, crystalline silica, and zirconium. Said engobe is typically applied on the ceramic semi-finished product in an amount between 460 and 880 g/m² at a density between 1200 and 1500 g/litre (dry equivalent: from 210 to 440 g/m²). Alternatively, or in addition, said composite is applied during the glazing step, for example in amounts between 100-300 g/m².

Alternatively, said functionalized and oriented composite is added to the ceramic mixture, obtaining an enriched ceramic mixture. When said functionalized composite is mixed with a ceramic mixture, said functionalized composite is added in a percentage of 10-50% w/v, preferably 20%. After moulding, said enriched ceramic mixture gives rise to a ceramic semi-finished product that comprises the oriented functionalized composite.

The ceramic semi-finished product that comprises the oriented functionalized composite is then submitted to a baking cycle at temperatures between 600 and 1400° C., preferably between 900 and 1300° C.

The duration of said baking cycle is closely linked to the thickness of the ceramic semi-finished product, where the baking times get longer with increase in thickness. Merely as an example, 60×60 tiles with a thickness of 10 mm require a baking cycle of about 40 minutes. Keeping the same surface area but increasing the thickness to 20 mm, the baking times required increase to about 90 minutes.

The present inventors have demonstrated, surprisingly, that after said baking, said biomimetic material and/or biomaterial passes from a nanometric state to a nanostructured micrometric state.

The ceramic material thus obtained advantageously comprises a crystalline material that has the diffraction maxima characteristic of rutile. X-ray diffraction, spectrum in FIG. 3A, shows the principal phases present: rutile (R), quartz (Q), mullite (M), anorthite (A), wollastonite (W).

Figure 4A:
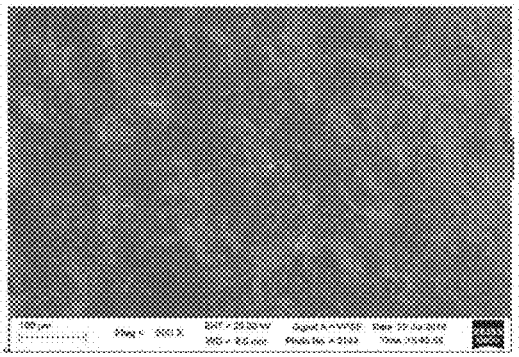
FIGS. 4A, 4B, 4C and 4D: examination by scanning electron microscope (SEM) of the photocatalytic, active ceramic surface according to the present invention.
Figure 4B:
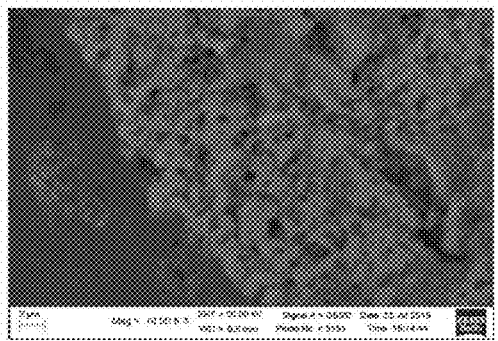
Figure 4C:
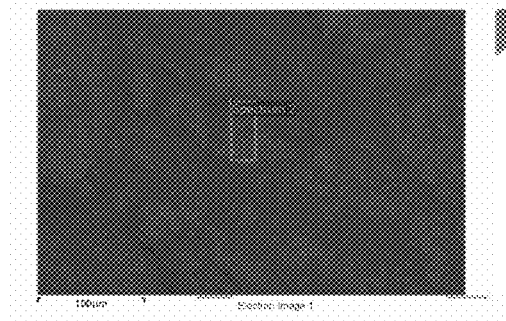
Figure 4D:
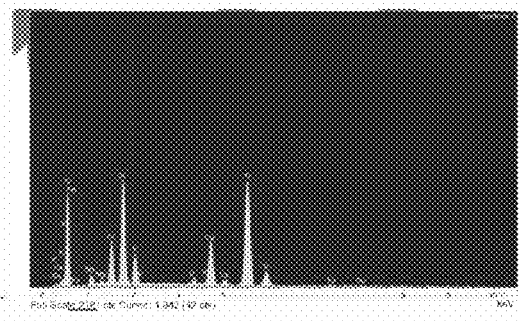

Examination with the scanning electron microscope (SEM) shows, as shown in FIG. 4A, that hydroxyapatite microcrystals were obtained with a nanostructured hierarchical structure, constituted of rutile at the surface (FIG. 4B), indicating that baking has modified the hydroxyapatite from nanometric to nanostructured micrometric. The particles all have a micrometric size; the distribution ranges from about 1 to 100 micrometres. The spectrum obtained in EDS microanalysis (FIGS. 4C and 4D) shows that the elemental composition of the particles consists of calcium and phosphorus in a ratio compatible with that of hydroxyapatite. Moreover, the signal of titanium and that of oxygen are noted. The particles analysed at different points give the same composition, supporting the fact that a hydroxyapatite-rutile aggregate has formed.

In a further embodiment, the present invention relates to a photocatalytic ceramic material endowed with antibacterial activity, where said ceramic material is characterized in that it comprises hydroxyapatite microcrystals with a nanostructured hierarchical structure with macro and micro cavities. Within said microcavities, $TiO_2$ is included in the rutile crystalline form.

Figure 3A:
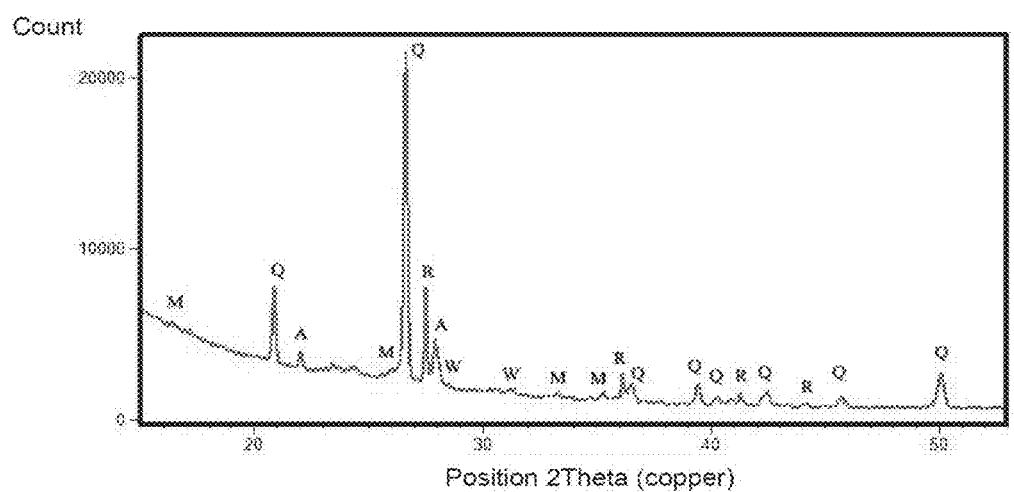
FIG. 3A: X-ray diffraction spectrum of the photocatalytic, active ceramic surface according to the present invention.
Figure 3B:
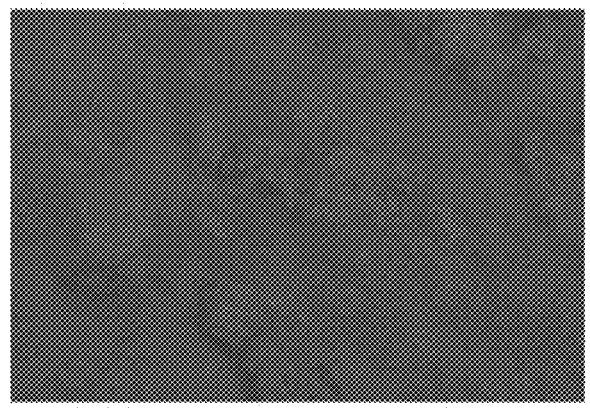
FIG. 3B: surface mapping, obtained by EDS spectroscopy (Energy Dispersive X-ray Spectrometry), of the photocatalytic, active ceramic surface according to the present invention.
Figure 3C:
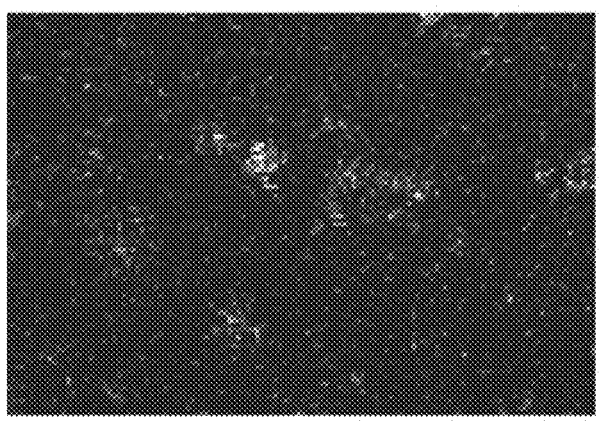
Figure 3C:
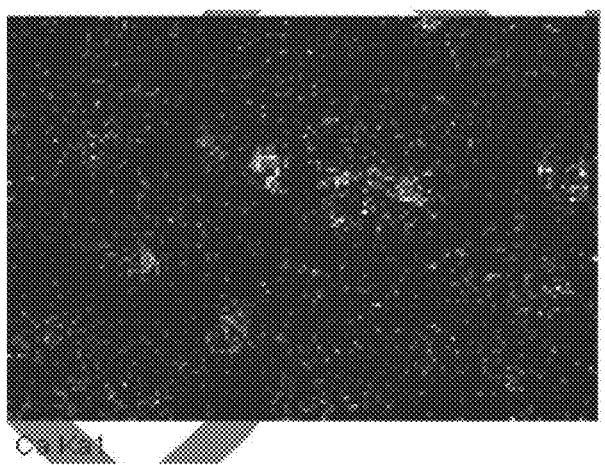
Figure 3E:
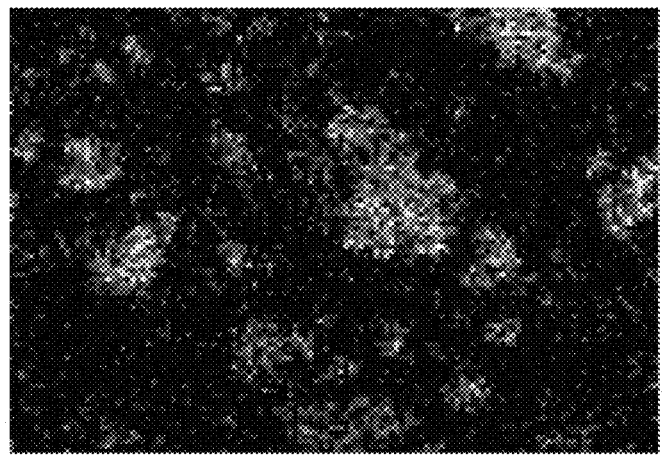

Said ceramic material is characterized by the X-ray diffraction spectrum as in FIG. 3A and by surface mapping of the atoms present in the ceramic material, obtained by means of "mapper EDS" or EDS spectroscopy (Energy Dispersive X-ray Spectrometry) that utilizes the emission of X-rays generated by an accelerated electron beam when it hits the ceramic sample, as in FIG. 3B. The images highlight that the localization of the titanium atoms (FIG. 3E) is substantially superimposable on that of the phosphorus and calcium atoms (FIGS. 3C and 3D, respectively), where said phosphorus and calcium atoms belong to the hydroxyapatite, which is in fact functionalized with titanium.

For comparative purposes, the photocatalytic activity of a photocatalytic ceramic material according to the present invention (a) was compared with that of a commercial photocatalytic ceramic material that comprises anatase (b).

The test involved measuring the amount of methylene blue before and after irradiating the material with a mercury vapour lamp.

Figure 5A:
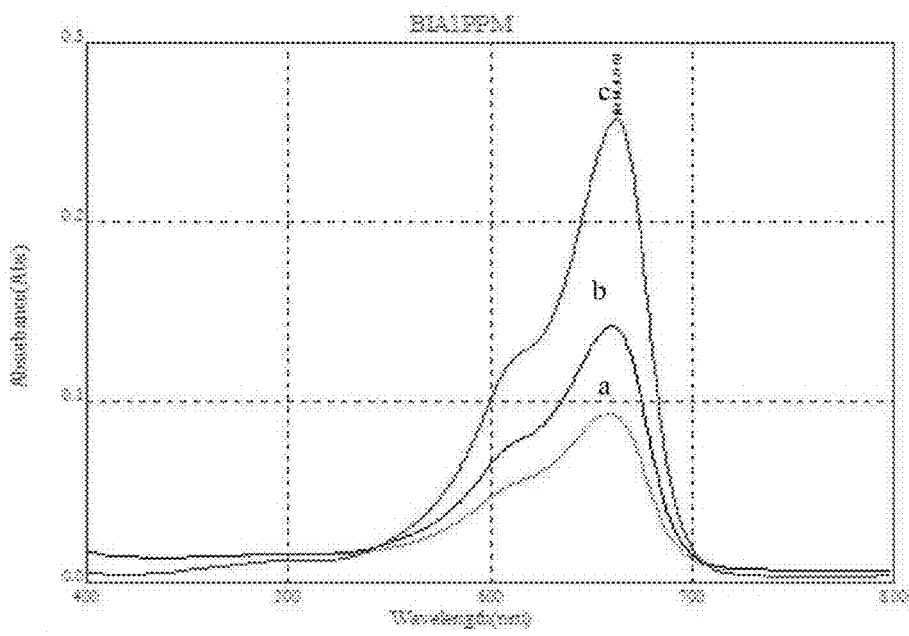
FIGS. 5A and 5B: comparative test of photocatalytic activity at 12 hours (FIG. 5A) and at 48 hours (FIG. 5B) of a photocatalytic ceramic material according to the present invention (a) or of a commercial photocatalytic material that comprises anatase (b). Curve (c) relates to the result obtained on a non-photocatalytic surface.
Figure 5B:
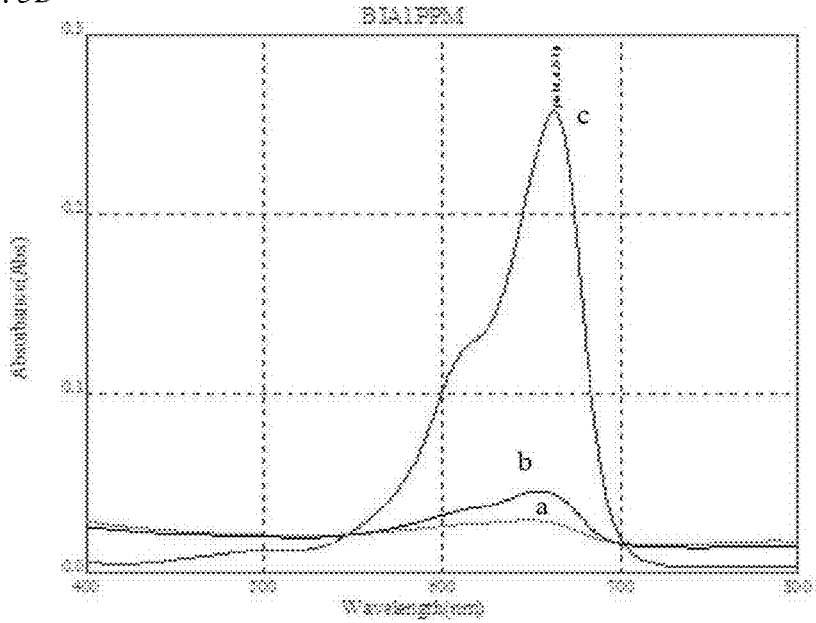

Surfaces (a) and (b) were covered with an equal volume of a 1 ppm solution of methylene blue and they were irradiated for 12 hours. The diagram in FIG. 5A shows, curve (a), the extraordinary photocatalytic activity of the ceramic material according to the present invention. On prolonging the irradiation to 48 hours, the difference is still significant (FIG. 5B, curve a). Curve (c) shows, in both diagrams, a non-photocatalytic surface covered with the same volume of a 1 ppm solution of methylene blue.

Surprisingly, the present inventors have developed an innovative "bio-inspired" ceramic material and a method for producing it efficiently.

The innovative technique according to the present invention in fact envisages a single baking step, i.e. baking once in a first firing.

With the technique according to the present invention, biomimetic microcrystals are obtained that have a hierarchical macro and microporous structure after baking, said microcrystals having a morphology and dimensions that make them extremely reactive and available for binding with rutile, which is crystallized starting from amorphous Ti inside and outside said microporous structure. The experimental data obtained, and reported here, show the high photocatalytic, antibacterial and anti-contamination activity of the ceramic material according to the present invention. The macro and micro cavities present in the hierarchical structure characterizing the ceramic material according to the present invention function as reaction chambers or centres. Contaminating organic substances are trapped and then degraded therein, when the surface is exposed to wavelengths in the visible.

Among the known crystalline forms of $TiO_2$, rutile is the thermodynamically most stable natural form, as well as being the only form that is activated at wavelengths in the visible. Addition of metal during preparation permits doping of the titanium, which mainly activates it at wavelengths in the visible region.

Advantageously, the ceramic according to the present invention does not lose the antibacterial and anti-contamination activity over time, since nHA/amorphous Ti, deposited on the ceramic semi-finished product or added to the ceramic mixture, undergoes a heat treatment at high temperatures, i.e. above 600° C., sufficient to "weld" it to the ceramic, making it resistant to abrasion. The examples that follow are purely for the purpose of better illustrating the invention and are not to be understood as limiting it, its scope being defined by the claims.

Example 1: Synthesis of HA+Ti (Basic Hydrolysis)

Preparation of hydroxyapatite nHA: 16 ml of 1.35 M calcium hydroxide is added to 70 ml of water and is neutralized with 10 ml of 1.26 M phosphoric acid. The pH is adjusted to 11 with about 4 ml of 1 M sodium hydroxide. A hydrolysis suspension based on nanocrystalline hydroxyapatite is obtained.

Suspension of amorphous Ti: 0.1-0.5% w/v of one or more metal ions selected from Cu, Zn, Ag, Sr, Al, solvated with 10-30% of isopropyl alcohol or alternatively ethyl alcohol and 10-30% w/v of amorphous Ti.

nHA functionalized with amorphous Ti is obtained by adding, slowly and while stirring vigorously, said suspension of amorphous Ti, in an amount between 20-60% w/v, to said hydrolysis suspension.

Example 2: Synthesis of TCP+Ti (Basic Hydrolysis)

Preparation of hydroxyapatite β-TCP, Ca/P ratio 1.30-1.55 preferably 1.51: 14 ml of 1.35 M calcium hydroxide is added to 70 ml of water and is neutralized with 10 ml of 1.26 M phosphoric acid. The final pH should be between 7 and 11, preferably 8. A hydrolysis suspension is obtained.

Suspension of amorphous Ti: 0.1-0.5% w/v of one or more metal ions selected from Cu, Zn, Ag, Sr, Al, solvated with 10-30% of isopropyl alcohol or alternatively ethyl alcohol and 10-30% w/v of amorphous Ti.

Said suspension of amorphous Ti is added, slowly and while stirring vigorously, to said hydrolysis suspension, obtaining hydroxyapatite functionalized with amorphous Ti.

Example 3: Brushite Synthesis (Acid Hydrolysis)

To prepare 100 ml of a suspension of brushite and/or monetite ($CaHPO_4 \cdot 2H_2O$ (brushite) and $CaHPO_4$ (monetite)), 16 ml of 1.35 M calcium hydroxide is added to 70 ml of water and is neutralized with 10 ml of 1.26 M phosphoric acid. The final pH should be between 4 and 7, preferably 6. A suspension of amorphous Ti constituted as follows: 0.1-0.5% w/v of one metal ion, or mixture thereof in 1/1 ratio, of Cu, Zn, Ag, Sr, Al and solvated with 10-30% of isopropyl alcohol or alternatively ethyl alcohol and 10-30% w/v of amorphous Ti, are added, slowly and while stirring vigorously, to said hydrolysis suspension.

nHA functionalized with amorphous Ti is thus obtained.

Example 4: Mixture with Engobe

Functionalized nHA as from examples 1-3, which is the functionalized and oriented composite, is added to the engobe mixture in percentages of 10-50% w/v and applied on a ceramic semi-finished product in an amount between 460 and 880 $g/m^2$ at a density between 1200 and 1500 g/litre (dry equivalent: from 210 to 440 $g/m^2$). Said engobe comprises kaolin, crystalline silica, zirconium. Said coated ceramic semi-finished product is then exposed to baking in a first firing, at temperatures between 900 and 1300° C.

Example 5: Mixture with Salt Glazing

Functionalized nHA as from examples 1-3, which is the functionalized and oriented composite, is added to the mixture of salt glazing in percentages of 10-50% w/v and applied on the ceramic product that has not yet undergone the baking process in amounts: from 260 to 360 $g/m^2$ at a density from 1100 to 1500 g/litre (dry equivalent: from 110 to 170 $g/m^2$). Said salt glazing mixture comprises ceramic frits, crystalline silica, kaolin. Said coated ceramic semi-finished product is then exposed to baking in a first firing, at temperatures between 900 and 1300° C.

The invention claimed is:

1. A method for producing an antibacterial photocatalytic ceramic, said method comprising:
    (a) providing an amorphous compound containing titanium;
    (b) providing a biomimetic material or a biomaterial, said biomaterial comprising calcium phosphate or said biomimetic material comprising calcium phosphate;
    (c) functionalizing said biomimetic material or said biomaterial with said amorphous compound containing titanium to obtain a functionalized and oriented composite, where oriented means having a crystal structure;
    (d) adding said functionalized composite to a ceramic mixture, and/or applying said functionalized composite on a ceramic semi-finished product, where ceramic semi-finished product means the ceramic material before heating; and
    (e) heating at a temperature between 900 and 1300° C. for a time that varies from 20 to 500 minutes, to obtain an antibacterial photocatalytic ceramic.

2. The method according to claim 1, wherein the amorphous compound containing titanium is selected from the group consisting of at least one of: titanium(IV) oxysulphate, titanium tetrachloride, titanium tetraisopropoxide, titanium isopropoxide, and titanium oxychloride.

3. The method according to claim 1, wherein said biomimetic material or biomaterial is selected from the group consisting of brushite, monetite, hydroxyapatite (nHA), and (β/α) tricalcium phosphate (TCP) and having less calcium on the surface than inside the material or biomaterial.

4. The method according to claim 1, wherein in step (b), a biomimetic material is provided, and said biomimetic material is nanocrystalline hydroxyapatite (nHA) obtained at a pH between 7 and 14, by neutralizing a suspension of calcium hydroxide or calcium acetate or calcium chloride or calcium nitrate drop by drop with phosphoric acid under vigorous stirring for 2-12 hours.

5. The method according to claim 4, wherein said nHA has a molar ratio between surface Ca/P in the range from 1.55 and 1.70.

6. The method according to claim 1, wherein said functionalization is carried out by adding said amorphous compound containing titanium dropwise to a solution of calcium phosphate in the form of brushite and/or monetite in the case of acid hydrolysis (pH 1-6), or in the form of nHA or (P/a) TCP in the case of basic hydrolysis (pH 7-14).

7. The method according to claim 1, wherein said functionalization is carried out with doped titanium and said amorphous compound containing titanium is added dropwise in suspension with one or more solvated metal ions selected from the group consisting of Cu, Zn, Ag, Sr, Al, Sb, W, Mn, Sn, V, Cr, Zr, Mo, and Pd.

8. The method according to claim 1, wherein said oriented functionalized composite is applied on a ceramic semi-finished product simultaneously with one or more glazing applications, or mixed with engobe applied after the forming step, or between one or more glazing applications and/or during the process of screen printing, and/or of salt glazing.

9. The method according to claim 4, wherein said pH is pH 11.

10. The method according to claim 5, wherein said molar ratio between surface Ca/P is 1.64.

* * * * *